US006915805B2

(12) United States Patent
Crutchfield

(10) Patent No.: US 6,915,805 B2
(45) Date of Patent: Jul. 12, 2005

(54) PADDED X-RAY COMPATIBLE SPINE BOARD

(76) Inventor: John Stuart Crutchfield, 1705 Royal Oak Dr., Tyler, TX (US) 75703

( * ) Notice: Subject to any disclaimer, the term of this patent is extended or adjusted under 35 U.S.C. 154(b) by 85 days.

(21) Appl. No.: 10/417,001

(22) Filed: Apr. 16, 2003

(65) Prior Publication Data

US 2003/0200972 A1 Oct. 30, 2003

Related U.S. Application Data

(60) Provisional application No. 60/375,956, filed on Apr. 26, 2002.

(51) Int. Cl.[7] .................................................. A61F 5/37

(52) U.S. Cl. ................................ 128/870; 5/624; 5/625

(58) Field of Search ................................ 128/845, 869, 128/870, 876; 5/624, 628, 82 R, 630, 636, 637, 625, 627, 621

(56) References Cited

U.S. PATENT DOCUMENTS 3,938,204 A * 2/1976 Slominski ...................... 5/255
4,506,664 A * 3/1985 Brault .......................... 5/82 R
5,016,620 A * 5/1991 Matthews ................... 128/870
D328,351 S 7/1992 Ott
D358,652 S 5/1995 Pretzer
5,560,059 A * 10/1996 McQueen ...................... 5/625
5,568,662 A * 10/1996 Gougelet ....................... 5/625
5,771,513 A 6/1998 Kirchgeorg et al. ........... 5/625
5,950,627 A * 9/1999 Bologovsky ................ 128/869
6,138,306 A * 10/2000 Muhanna ....................... 5/626
6,427,695 B1 * 8/2002 Zanetti ....................... 128/846
D471,634 S 3/2003 Crutchfield

* cited by examiner

*Primary Examiner*—Michael A. Brown
(74) *Attorney, Agent, or Firm*—C. W. Alworth

(57) ABSTRACT

A molded plastic spine board having specialized padding strategically located in the board and stiffing members. The specialized padding reduces patient discomfort and aids perfusion in the regions that are in contact with the board while the patient is immobilized on the board thereby helping to prevent tissue ischemia and pressure ulcer formation. The stiffening members strengthen the board eliminating deflection of the board thereby keeping the patient immobilized while eliminating artifacts (shadows and interference) in x-rays thereby ensuring good x-ray examination.

26 Claims, 12 Drawing Sheets

DETAIL D

PADDED X-RAY COMPATIBLE SPINE BOARD

This application claims priority from U.S. Provisional Application Ser. No. 60/375,956 filed on Apr. 26, 2002.

TECHNICAL FIELD OF THE INVENTION

This device relates generally to the medical community and in particular to an extraction, transportation and immobilization board for use by emergency medical personnel that helps prevent injury to the spine of an immobilized patient while allowing treatments and x-rays to be made or taken on the immobilized patient without generating interference patterns on the x-ray results. The device has strategically located padding in the board that improves the patient comfort level and helps to prevent tissue ischemia and pressure ulcer formation.

BACKGROUND OF THE INVENTION

Extraction, transportation and immobilization boards are used in the medical community for transporting trauma victims. Emergency medical personnel will strap the victim to an immobilization board (backboard) whenever they know or suspect that the victim's spine has been injured. This technique is used to minimize the chance of further injury to the spine while the victim is being extracted or transported from the scene. In fact, the victim is often immobilized for hours on the backboard during transportation to the hospital and while awaiting diagnostic studies.

The practice of strapping the victim to these immobilization boards stems from the fact that many trauma victims sustained additional neurological injuries because of undiagnosed spinal instability while the victim was being lifted or carried to ambulances and hospitals. Backboards help prevent additional injuries by keeping the vertebrae aligned so as not to further compress the spinal cord and nerves which lie within a small opening in the spine, known as the vertebral canal. The victim will be left strapped to the backboard for hours during transportation to emergency facilities and while undergoing initial examination at an emergency facility.

The victim will not be taken from the backboard until the victim's spine is examined by a medical specialist (generally a neurosurgeon) who will "clear" the victim prior to the removal of the victim from the backboard. The process of "clearing" the victim involves examination of the victim (patient) and examination of x-rays. This procedure can take hours before a determination can be made of whether or not the patient can safely be removed from the backboard.

The inability to move for hours on end leads to great discomfort and, quite often, great pain for the patient. Patients have complained of pain at the back of the skull (occiput), shoulder blades (scapulas), mid back area (thoracic kyphosis), tailbone (sacrum and coccyx), pelvic areas (posterior superior iliac spines) and heels (calcaneus). These areas of the body are the same areas that have the greatest contact with the backboard. The pain arises from the patient's inability to move and take pressure off of these areas (i.e., shift the body weight). In addition, the lack of movement compromises the blood flow (perfusion) in the tissues in these regions during the period of immobilization. The compromised perfusion leads to tissue ischemia that in turn causes pain. The tissue ischemia often leads to "pressure ulcers" (decubitus ulcers). The development of these ulcers often leads to an increase in the patient's morbidity, an associated increase in the length and cost of hospitalization and to increase in the possibility of surgery or similar additional treatment.

The current art in backboards has undergone little change with regard to the above expressed concerns. It appears that backboards are designed, built and sold with a view toward cost and durability. Current improvements center about the use of stronger and more lightweight materials in order to increase the carrying capacity and decrease the load that ambulances, paramedics, and attendants must carry. Other improvements have focused on craniocervical stabilization, universal padding, addition of wheels to the backboard, folding backboards, floatable backboards, and the like. The art has not concentrated on improving patient comfort, reducing the chance of the formation of pressures ulcers, increasing tissue perfusion, and the like while the patient is immobilized on the backboard.

For example McQueen, U.S. Pat. No. 5,560,059, discloses a patient stretcher containing inflatable supports located under the neck and torso of immobilized patient. The McQueen stretcher is formed from rigid polymeric materials that incorporate a pair of depressions that contain the inflatable pads. Close inspection of the drawings show that if x-rays are taken with the patient on the board, reflection and interference will occur due to the stiffening supports associated with the stretcher. Furthermore, the inflatable pads can cause movement of the patient thus negating the effect of the spine board, and no padding is provided for the lower extremities (legs/feet).

Bologovsky et al., U.S. Pat. No. 5,950,627, disclose a spine board manufactured from a molded urethane-filled polymer shell that is stiffened with a series of carbon filament tubes. The Bologovsky device makes no effort to provide padding and states that board is x-ray transparent with the exception of the stiffening elements.

The prior art includes a series of design patents that attempt to meet the requirement for a lightweight stiff spine board. See for example, Pretzer, U.S. Pat. Des. No. 358,652 that shows no padding and Ott, U.S. Pat. Des. No. 328,351 that shows padding for only the feet. The inventor (Crutchfield) discloses a spine board, see U.S. Pat. No. Des. 471,634, that illustrates a padding system for the head/spine/torso and the legs/feet. Whereas the Crutchfield design provides padding and a stiff spine board, it was discovered that the board showed minor flexing and in particular caused interference in x-ray pictures due to the increased density of the stiffening members: like the Bologovsky device.

Kirchgeorg et al., U.S. Pat. No. 5,771,513 discloses an x-ray compatible, partially flexible patient support. The Kirchgeorg device is essentially a flexible support that wraps from one side of the patient to the other thereby retraining the patient in a blanket like structure that is stiff from the head to the feet. Some motion is still possible (hence the title "partially flexible") which prohibits the use of the device in a patient suffering severe spinal injury.

Thus there remains a need for a carefully designed backboard that is lightweight and stiff but contains strategically located pads to reduce patient discomfort, decrease the likelihood of compromised tissue blood flow (perfusion) in pressure regions leading to an overall reduction in pain and the formation of pressure ulcers while allowing x-ray examination without interference or shadowing.

SUMMARY OF THE INVENTION

The instant backboard is designed to provide appropriate padding that follows the contour of the pressure points in the pattern of an immobilized supine human skeleton of average stature. It is known that the instant device cannot perfectly fit all humans because no one human is “average” and therefore there is no standard proportion. The instant device has cushioned pads at optimum locations on the board in order to meet the objectives stated above.

Additional modifications included in the design of this board are openings in the undersurface railings designed to permit placement of a standard chest X-ray cassette in order to facilitate taking an anterior-posterior chest X-ray without lifting the patient. Small openings about the outer perimeter are also provided to secure intravenous poles and keep the ambulance attendants hands free of this task.

The backboard is manufactured using standard molding techniques in two halves that are joined together using standard techniques. A stiffening channel is molded about the outer perimeter of the board in the upper and lower halves. Underside railings are formed in the lower half as an additional stiffening channel in a position that minimizes and/or eliminates the chance of causing artifacts on X-rays. These railings like the current art, allow the spine board to readily slide along other surfaces (gurneys, platforms, and the like).

The underside of the board, where the torso and head will lie, has a carefully designed v-groove stiffening pattern incorporated as part of the lower mold. The v-groove angles are chosen to minimize and/or eliminate x-ray interference (shadowing or causing artifacts); thereby, minimizing or eliminating x-ray interference in the most critical area of the patient—the spine which includes the neck. Thus, the thermoplastic spine board is fully stiffened by the perimeter channel (essentially a box channel), the two rail channels (a modified box channel) and the underside v-grooves.

Carefully placed openings along the edges of the board allow for comfortable handgrips and for the attachment of immobilization belts, without compromising the strength of the backboard. Additional openings are provided for restraint belts in the leg area of the board. The board is easily cleaned and the cushions may be replaced to prevent transmission of pathogens transmitted by body fluids.

Thus the instant device provides a lightweight stiff backboard that is compatible with hospital x-ray and other scanner-type machines (MRI, etc.) and provides padded areas thereby reducing patient discomfort, decreasing the likelihood of compromised tissue blood flow (perfusion) in pressure regions, and leading to an overall reduction in pain and formation of pressure ulcers while allowing x-ray examination without interference or shadowing.

DESCRIPTION OF THE PREFERRED EMBODIMENT

This disclosure will first discuss the prototype device thereby tracing the development of the preferred device that will be fully disclosed.

The prototype device was manufactured from plastic using standard molding techniques and will be discussed in detail later in this disclosure. The outer plastic sheath is formed about a “filled interior.” In order to obtain the required stiffness (i.e., a backboard must not bend or deform with a patient in place) the plastic filled prototype interior was shaped in ridges, valleys and honeycombs; thus, when the outer plastic material was formed about the inner material the overall backboard become rigid. Wood reinforcement was used in the prototype however carbon fiber reinforcement could have been used or added to the interior.

It is known that great care has to be taken to ensure that the density of the material is as constant as possible to facilitate x-rays and scanner-type equipment used in hospital diagnostic equipment. (That is, the board must be essentially transparent or of constant opaqueness so that false readings will not be taken on the patient.) Furthermore, the placement of stiffening members (be they wood, carbon fiber or the like) should be carefully made in order to minimize interference with x-ray photography.

Unfortunately it was found that the prototype device—although providing a padded system that relieved patient discomfort, decreased the likelihood of compromised tissue blood flow (perfusion) in pressure regions, and lead to an overall reduction in pain and formation of pressure ulcers)—resulted in a slightly flexible board that would not properly immobilize a patient. Further, the prototype device caused minor, but fatal, artifacts (distortions and shadows) in the x-ray image caused by variations in board density (the urethane fill) and interference by support/stiffening members that were placed within the board (not shown). Thus, the prototype device leads to a completely new form of the spine board, while incorporating the special padded features of the prototype board.

The preferred device, 1, is shown in FIGS. 1 through 10 and is molded in two halves from Poly Carbonate/ABS plastic using standard molding techniques. The upper half and lower half do not quite lie on a mid point between the top and bottom of the assembled board as a result of molding and assembly techniques. (See FIGS. 9 and 10)

Figure 1:
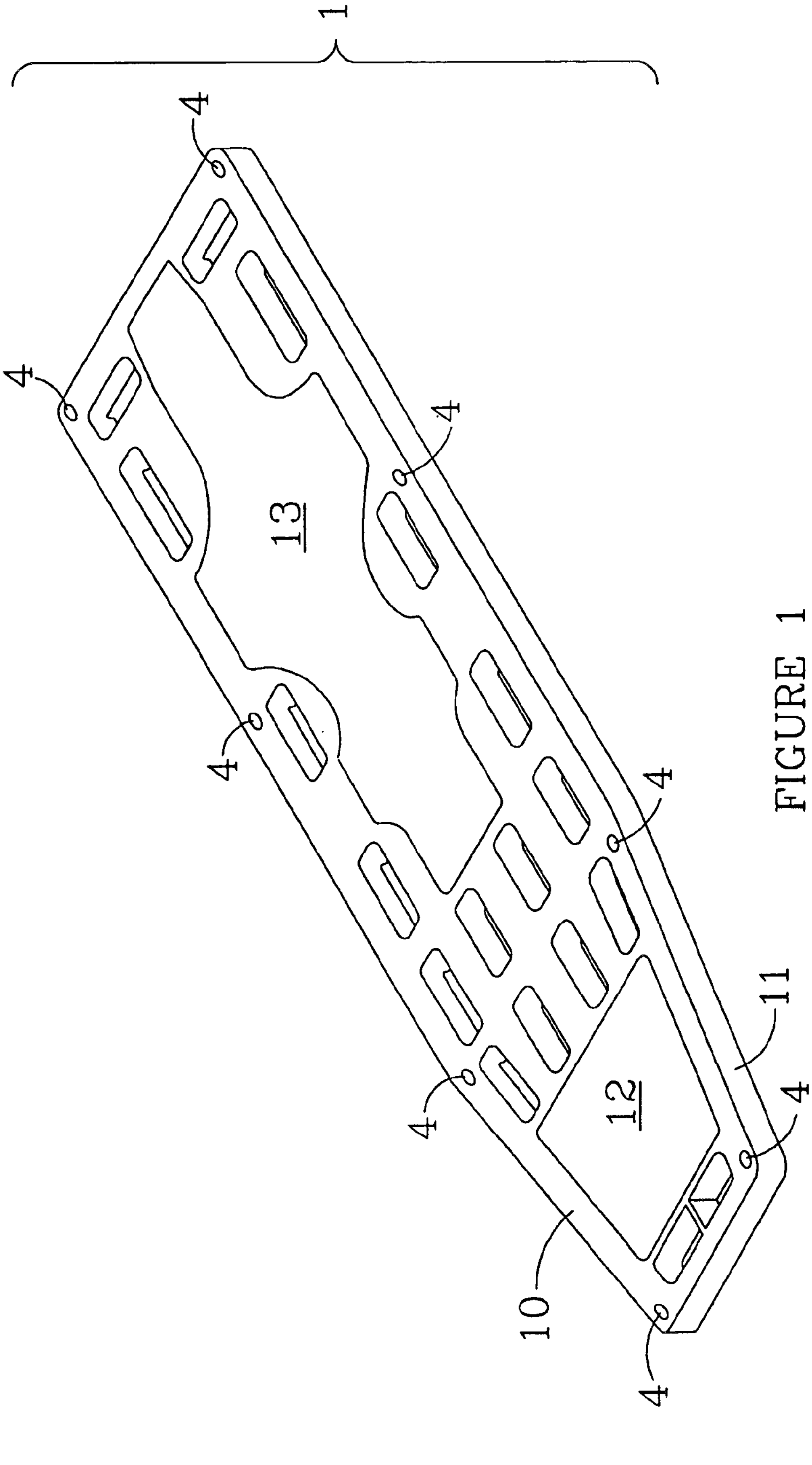
FIG. 1 is an isometric view of the instant device incorporating specialty pads showing the head end at the left hand side of the drawing.
Figure 2:
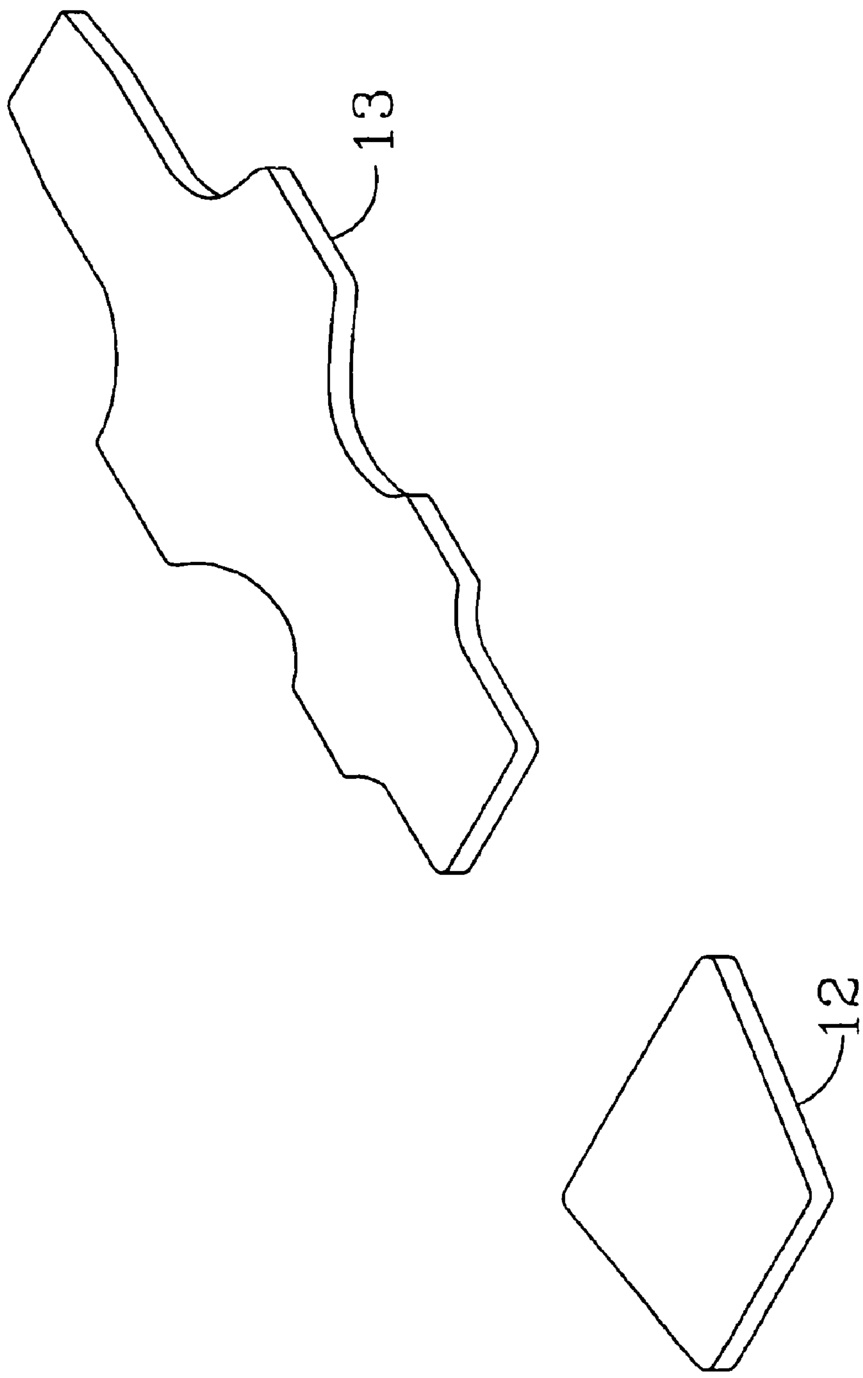
FIG. 2 is an isometric view of the specialty pads.
Figure 3:
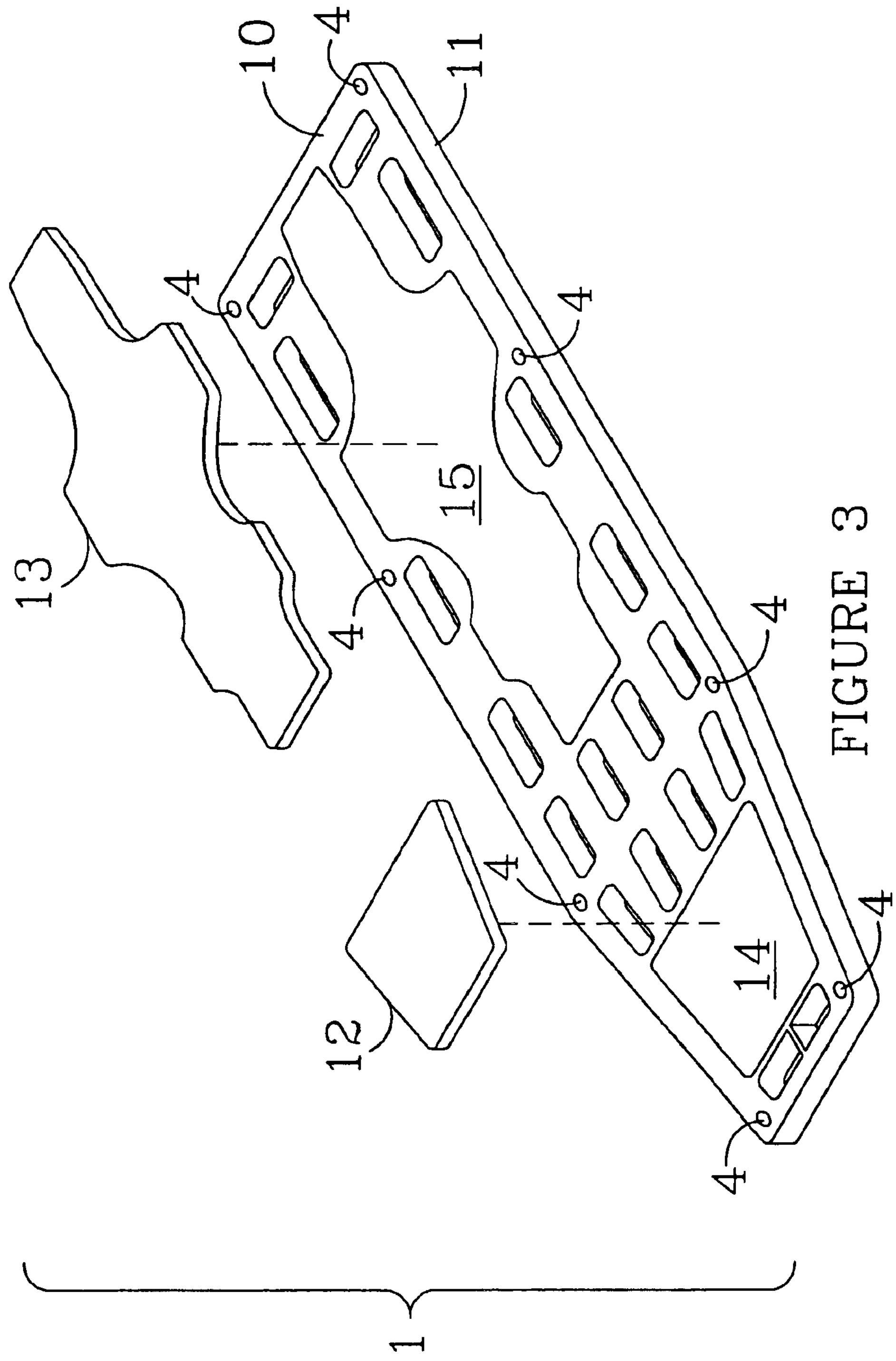
FIG. 3 is an exploded isometric view of the instant device showing the specialty pad design features and placement of the pads on the spine board.

The upper half or section, 10, contains indentions, 14 and 15, for the specialized pads, 12 and 13. The indentions are clearly shown in FIG. 3 and the pads are shown in FIGS. 1 and 2. The pads, 12 and 13, are manufactured from almost incompressible cushion material such as urethane. The pads must be sufficiently compressible so that a comfort level is attained, but sufficiently incompressible so that the patient’s spine is appropriately supported. The ideal material would be one that conforms to the body’s natural shape and remains in that state while the patient is immobilized. This material would ensure that the pressure exerted by the patient’s body weight would be spread out over as large an area as possible; thereby reducing the pressure in any one area. A modification of the “visco-elastic foam” developed by the National Aeronautics and Space Administration and used in certain commercial mattresses would be ideal, providing the material is made to be almost incompressible, i.e. a dense visco-elastic material.

As shown in FIG. 2, the heel/foot pad, 12, takes the shape of a quadrilateral and is designed to accept the heels of the patient. The strange shape allows for the accommodation of a variety of human sizes and serves to cushion the heels (calcaneus). The hourglass like torso pad, 13, serves to cushion the skull (occiput), shoulder blades (scapulas), mid back area (thoracic kyphosis), tailbone (sacrum and coccyx), and pelvic areas (posterior superior iliac spines). As further shown in FIG. 3 the heel/foot pad is received by the heel/foot pad indention, 12, and the torso pad is received by the torso pad indention, 15: both indentions are located in the upper section, 10.

The hourglass shape of the torso pad has been chosen to support the shoulders and other parts of the body, as described above, while keeping as much of the surface area of the. board clear of padding. The "clear" area allows the medical technician space to place equipment, run straps through strap holes described below, and generally perform emergency procedures. A fully padded board will not function as well as the disclosed pad shape. Again the strange shape has been chosen to accommodate the greatest variety of human sizes and shapes.

Figure 4:
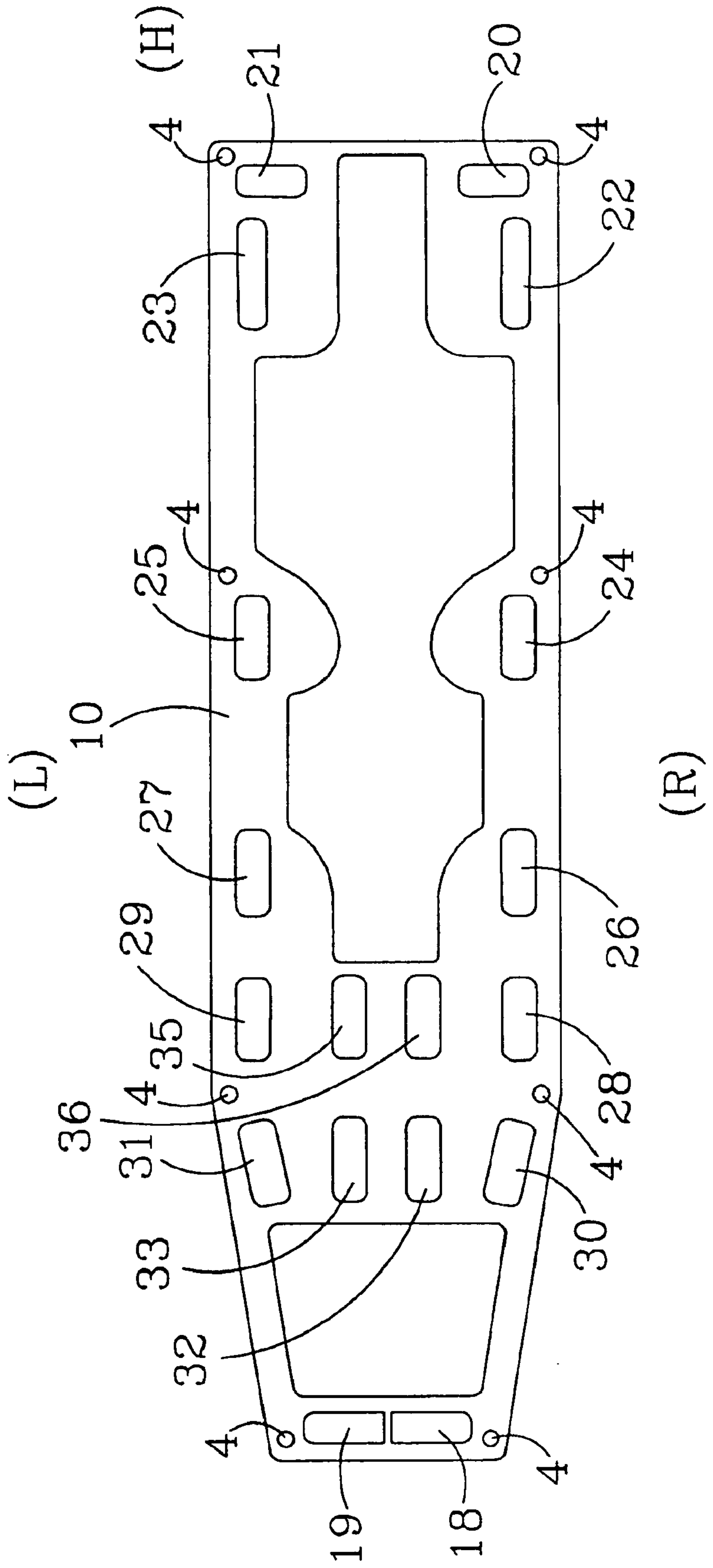
FIG. 4 is a top view of the instant device.

FIG. 4 is a top view of the instant device and shows the arrangement of the hand and/or strap/hand holds which consist of a plurality of openings (18–31) arranged around the perimeter of the device and a further plurality of openings (33–36) located between the foot/heel pad, 12, and the torso pad, 13. A majority of the openings about the perimeter jointly serve as strap holes or hand holds. The two openings at the rear of the device serve as hand holds: the right rear hand hold, 20, and the left rear hand hold, 19. Similarly the two openings at the head end (or front) of the board serve as hand holds: the right front hand hold, 20, and the left front hand hold, 21. Openings 22 and 23; 24 and 25; 26 and 27; 28 and 29; and 30 and 31 may also serve as hand holds or strap apertures (each forming a right and left respective pair of strap/hand holds—there being five such pairs shown). Openings 32 and 33; and 34 and 35 serve as mid strap apertures on the right and left sides respectively—there being two such pairs shown.

Figure 5:
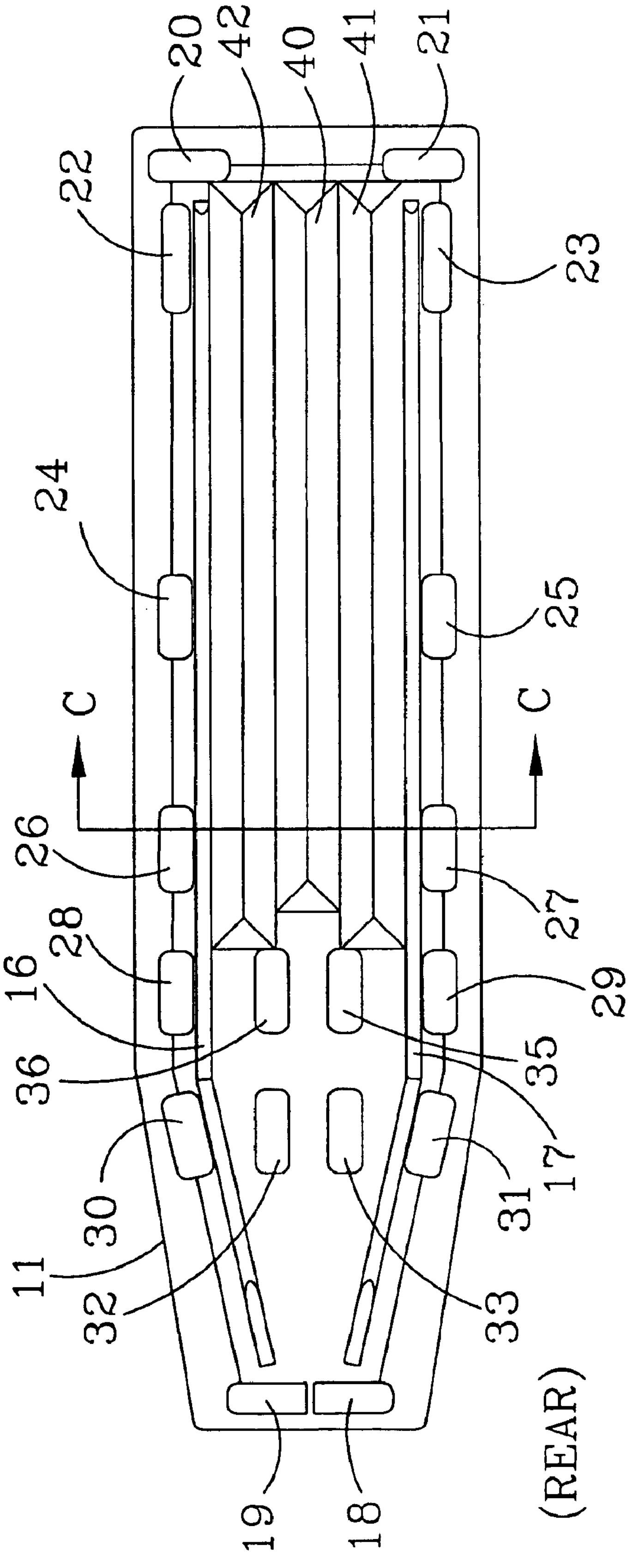
FIG. 5 is a bottom view of the instant device.

In a similar manner FIG. 5 is an underside view of the instant device showing the strap holes and hand holds/strap holes. FIG. 5 further shows a key element to the instant device and that is the V-channel stiffeners, 40, 41 and 42 that are molded into the lower section. The V-channel stiffeners are described in detail in paragraphs 45 and 49 below and are the element that stiffens the board.

Figure 6:
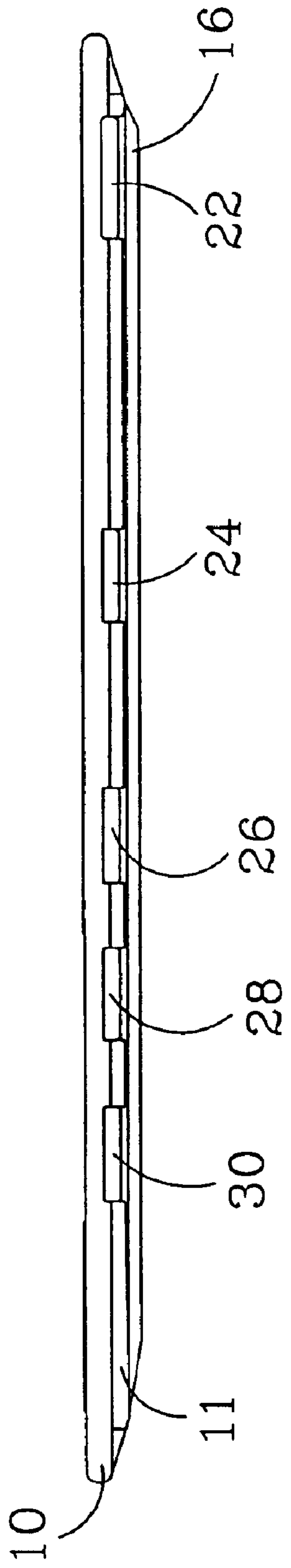
FIG. 6 is a side view of the instant device.

FIG. 6 is a side view of the instant device taken from the right side and further illustrates the location of the hand holds/strap holes (22, 24, 26, 28 and 30), the Right Side Skid, 16, and the boundary between the upper section, 10, and the lower section 11.

Figure 7:
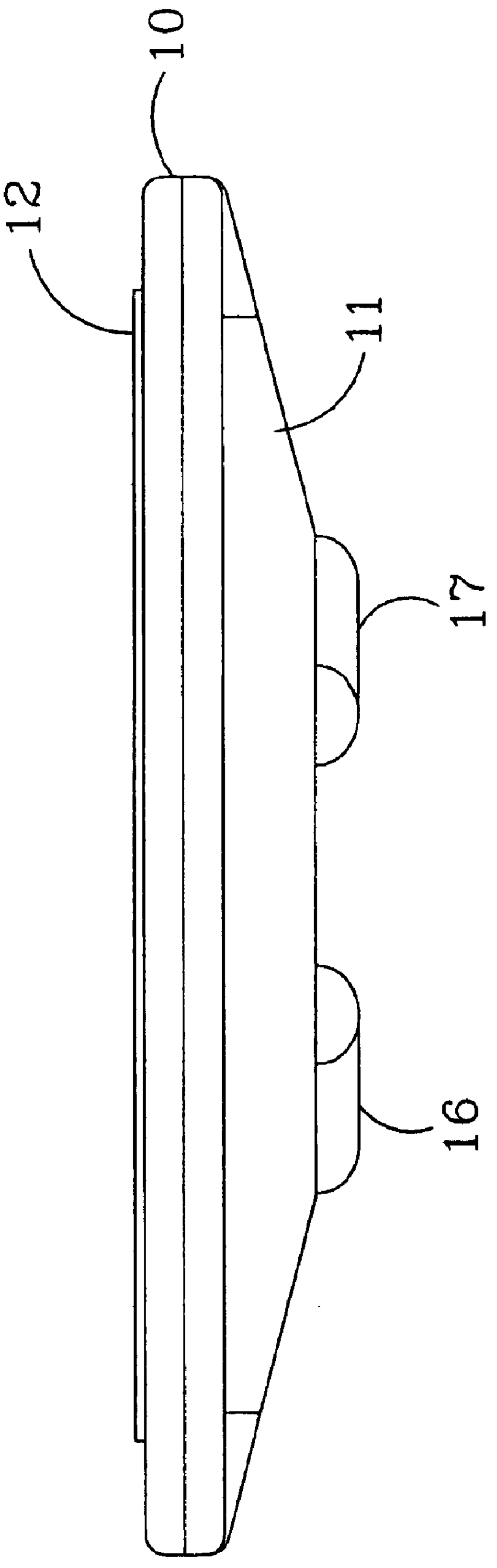
FIG. 7 is an end on view of the instant device taken from the head end.
Figure 8:
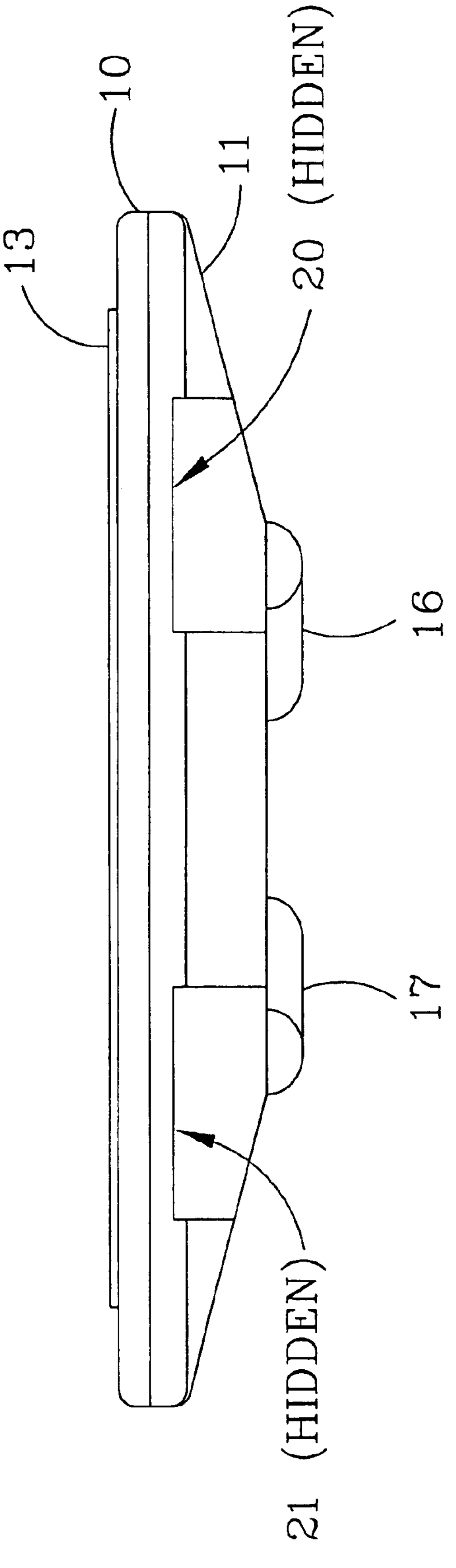
FIG. 8 is an end on view of the instant device taken from the foot end.

FIG. 7 shows an end on view of the instant device from the foot (rear) end. Two skids, 16 and 17, to be described later, are shown as well as the foot/heel pad, 12, described above. In a similar manner, FIG. 8 shows an end on view of the instant device from the head end/forward end. The two skids, 16 and 17, are shown as well as the torso pad, 13. The positions of the two front hand holds, 20 and 21 are shown (although marked as 'hidden'). In addition the upper, 10, and lower sections, 11, are shown.

Construction details for the preferred embodiment will be described using FIGS. 9 and 10; however, it should be realized that manufactures could readily deviate from these details. An upper perimeter stiffening L is molded around the entire outer perimeter of the upper section (or half) shown in FIGS. 9 and 10 as item 51 on the right side and continuing as item 61 on the left side. The L continues at the head and the foot of the board (not shown) with the same shape as shown in the FIGS. 9 and 10. As will be discussed the upper perimeter L mates with the lower perimeter L to form a perimeter stiffening channel shown in FIGS. 9 and 10 as items 50 (on the right side) and 60 (on the left side).

The perimeter-stiffening channel, as stated, extends from the outer edge of the board to just inside the outer perimeter hand/strap holds, 18 through 31. The perimeter-stiffening channel serves to stiffen the board about the outer perimeter and provide strength for the hand holds.

The lower half or section, II, contains a plurality of V-channel stiffeners, 40, 41 and 42, extending from the front-most mid strap apertures, 35 and 36, the front hand hold, 20 and 21. When the upper and lower sections are joined together, the V-channel stiffeners will lie more or less underneath the torso pad indention, 15, and run parallel to a longitudinal axis (V-channel axis) extending from the head to the foot of the board.

Figure 9:
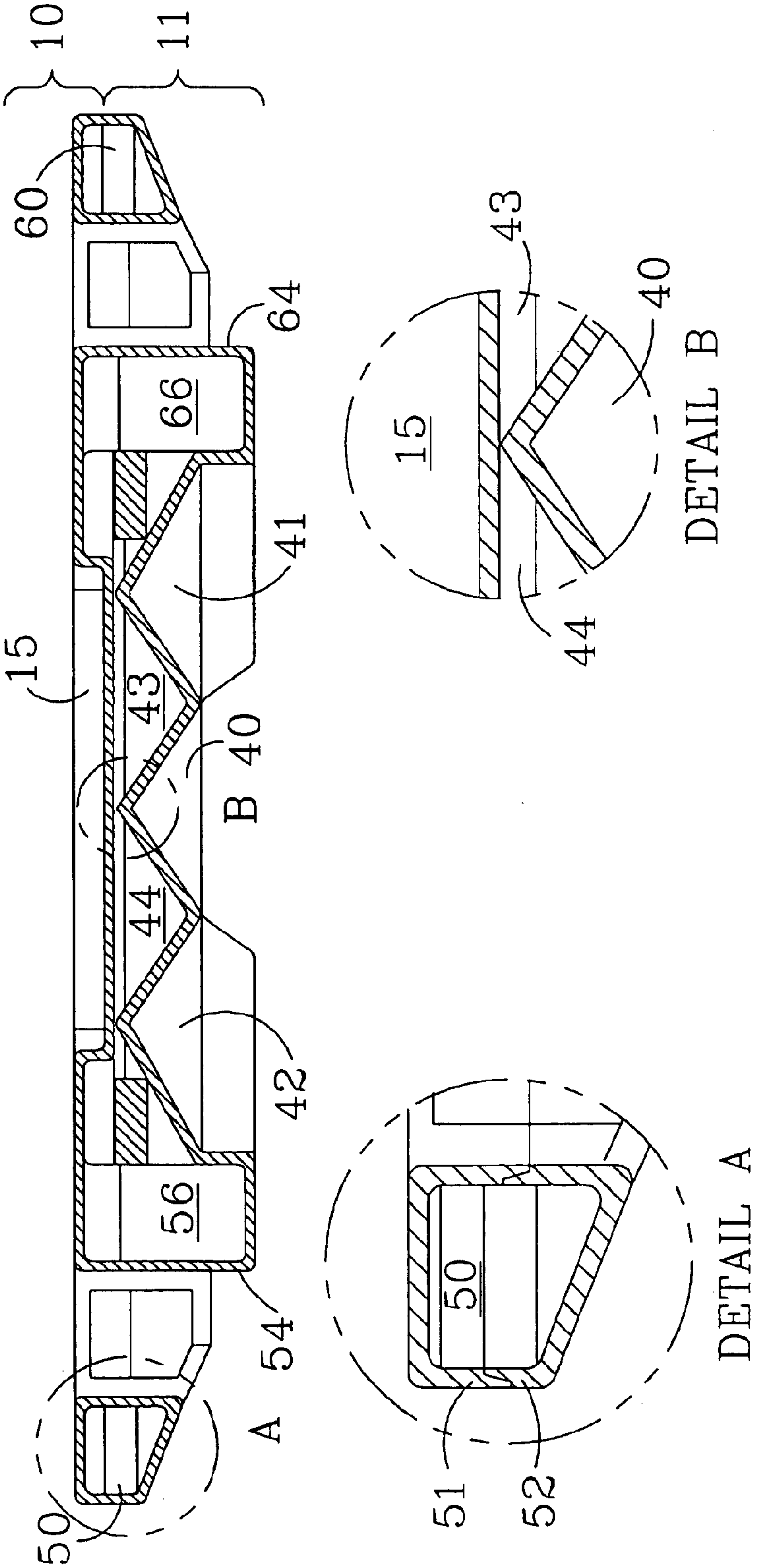
FIG. 9 is a cross-sectional view of the instant device taken at C—C in FIG. 5. Note the details A and B taken at the points shown in FIG. 9.
Figure 10:
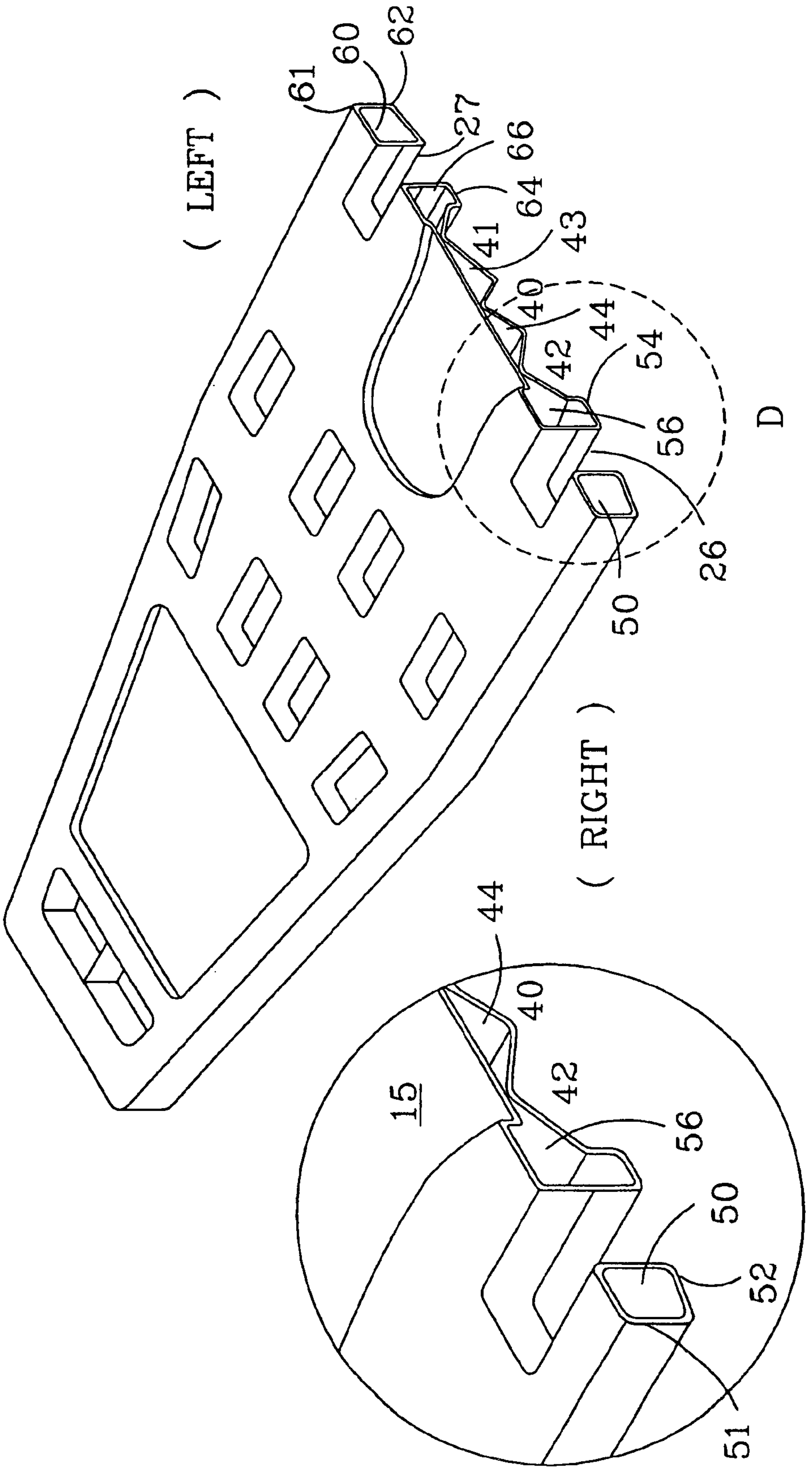
FIG. 10 is a cross-sectional isometric view of the instant device taken at C—C in FIG. 5. Note the detail D taken at the point shown in FIG. 10.

A lower perimeter stiffening L is molded around the entire outer perimeter of the lower section (or half) shown in FIGS. 9 and 10 as item 52 on the right side and continuing as item 62 on the left side. As with the upper section, the L continues at the head and the foot of the board (not shown) with the same shape as shown in the FIGS. 9 and 10. As will be discussed the lower perimeter L mates with the upper perimeter L to form an outer perimeter stiffening channel shown in FIGS. 9 and 10 as items 50 (on the right side) and 60 (on the left side).

Two lower rail stiffening U's are molded within the inner portion of the lower section along a longitudinal axis (rail axis) extending from the head to the foot just inboard of the outer perimeter hand/strap holes, 18 through 31, shown in FIGS. 9 and 10 as item 54 (on the right side) and 64 (on the left side).

The upper and lower sections (or halves) are connected together such that the upper and lower perimeter stiffening L's join together to form the perimeter stiffening channel. Furthermore, the undersides of the lower rail channels become the spine board skids. The lower plurality of V-channel stiffeners attach at their apex to the underside of the torso indention. All joints are secured using glue, thermal techniques or sonic techniques. In addition the hand hold halves are secured using glue, thermal or sonic techniques. The net result is a very stiffplastic spine board.

In designing the V-channel stiffeners, the molding engineer must assure that 45-degree angles are used throughout and that the apex of each channel be at 90-degrees to each of the sides of the channel. Thus, the width of the channel sides is set by the thickness of the plastic (set by strength of material considerations) and the requirement of the 45-degree angle. The 45-degree angle assures minimum shadowing of x-ray film. That is, the x-ray passes through the channel with little or no distortion.

The perimeter-stiffening channel, as stated, extends from the outer edge of the board to just inside the hand/strap holds, 18 through 31. The perimeter-stiffening channel serves to stiffen the board about the perimeter utilizing the properties of an "open box" beam and provides strength for the perimeter handholds.

The rail-stiffening channel, as stated, extends from just inboard of the hand/strap holes, 18 through 31, about the inner perimeter. The rail-stiffening channel forms the rail (or slide) on both bottom sides of the spine board while providing additional stiffening and strength to the board also utilizing the properties of an "open box" beam. In fact, the L-shaped perimeter channels may be formed as a U-shape. Thus, when the two halves are joined together the U's with mesh to form a closed box beam.

The rail stiffening channel forms an open box beam by incorporating the lower rail (54 and 64) and part of each of the outer V-channel stiffeners (41 and 42) as shown in FIG. 9. In a similar manner the V-channel stiffeners also use the principal of a box beam to provide stiffening. Two V-channel voids, 43 and 44 form a modified box beam with the underneath portion of the torso indentation as shown in FIG. 9.

Finally, the device provides a series of IV-apertures, 4, which are placed at strategic intervals about the outer perimeter of the upper half of the board. These apertures accept IV-stands that will hold IV-bags, other medical fluid distribution equipment or medical monitoring equipment. The IV-stands (not shown) when properly used will relieve the emergency medical provider of the additional duty of hold such items while attempting the carry the board.

A manufacturer will mostly likely provide varying sized boards. A standard board for most adults, a small board for small adults and a child board for children. The boards are lightweight and will take up little space in an emergency vehicle.

Additional stiffening materials such as carbon fiber may be incorporated in the perimeter channel during the molding process for the upper and lower halves of the board. And the perimeter channel may be filled with urethane foam. Similarly the rail channel may be reinforced using foam and/or carbon fiber. The area under the torso, neck spine and other body parts (arm, legs, etc) should be kept clear of material that could cause artifacts in x-rays.

Although the disclosure describes the rail stiffener as forming an open box beam by incorporating the lower rail (54 and 64) and part of each of the outer V-channel stiffeners (41 and 42) as shown in FIG. 9, it would be possible to bring the lower rail directly upwards and connect to the underside of the upper section. As claimed in the claims, the rail channel "box" structure can be omitted and regular stiff skids attached to the lower section. In a similar manner the disclosure describes the two V-channel voids, 43 and 44 as forming a modified box beam by connecting with the underneath portion of the torso indentation as shown in FIG. 9.

The inventor envisions an alternate embodiment without the torso and heel pads: under these circumstances the two channel voids would connect directly with the underside of the upper section. Furthermore, although the disclosure shows three V-channels, the number of channels will be set by the width of the board, the 45-degree requirement, the thickness of the plastic and the thickness of the final board. Such changes are within the disclosure.

Figure 11:
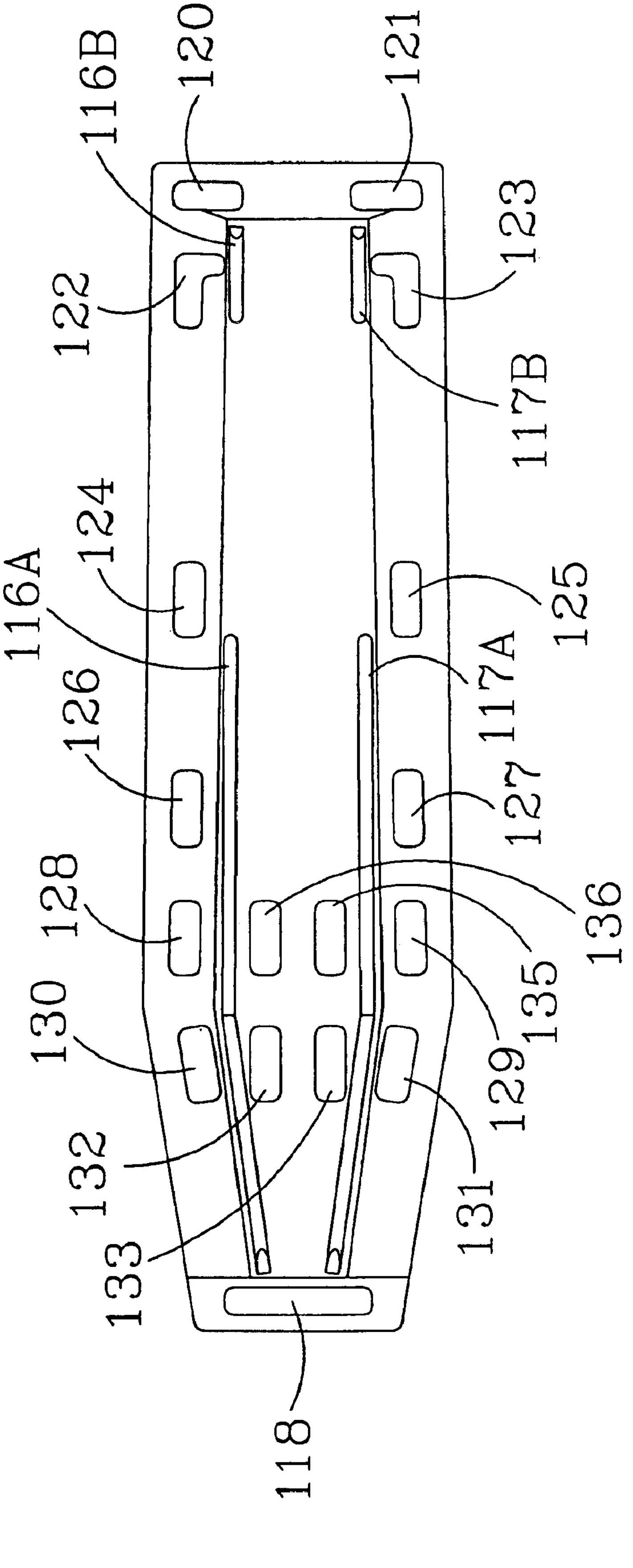
FIG. 11 is a bottom view of the initial prototype device.
Figure 12:
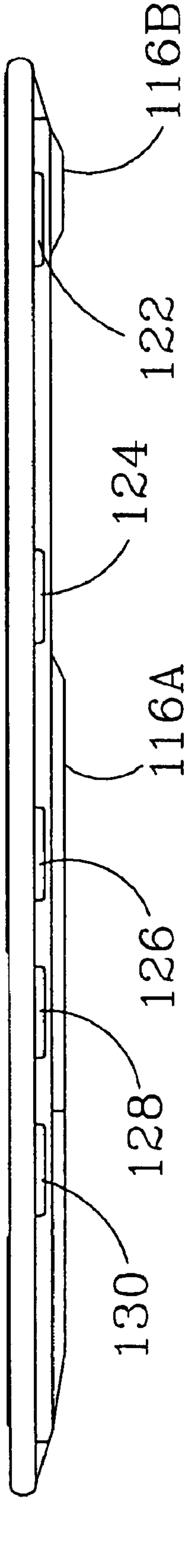
FIG. 12 is a side view of the initial prototype device.

The prototype device is shown in FIGS. 11 and 12, which are an underside view and a right side view with reference to the top view of FIG. 1. FIG. 1 is a top view of the preferred device, shown generally as item 1; however, the preferred device is very similar to the prototype device except for the shape of the rear handle slots and the front-most handle/strap slots. A plurality of openings or slots, 118 and 120 through 136, was formed in the prototype board. A majority of these openings are strap apertures, that is, the openings allow hold-down straps to pass through the opening(s) and around the patient: thereby, immobilizing the patient. (Standard trauma practice.) Openings 118, 120 and 121 serve as hand holds (118 serving as the rear hand hold and 120 and 121 serving as the right and left front hand holds respectively). Openings 122 and 123; 124 and 125; 126 and 127; 128 and 129; and 130 and 131 may also serve as hand holds or strap apertures (each forming a right and left respective pair of strap/hand holds—there being five such pairs shown). Openings 132 and 133; and 134 and 135 serve as mid strap apertures on the right and left sides respectively—there being two such pairs shown.

The prototype board was further stiffened using a pair of rails running from the rear of the board toward the front, 116A, 117A, that terminated at approximately the mid-point of the board and continued near the head of the board, 116B and 117B. The rails were placed as far away from the body location in order to reduce the chance of interference with x-ray photography/examination. These rails (or skids) also facilitate the grasping of the board by elevating it above ground level.

The same two specialized pads, which are shown in place in FIG. 1, are also used in the prototype, and the top of the prototype board had indentions specifically molded into the board to receive and hold these pads in place. The function and purpose of these two pads was discussed above when the preferred device was described. Additionally, a series of round Intravenous-apertures or IV-apertures, 4, were placed throughout the top surface. These IV-apertures, 4, are designed to accept metal rods that in turn can hold plasma bags, electronic monitoring equipment and other required medical equipment. This leaves the medical trauma technician free to concentrate on the patient (or carrying the board) while not having to hold onto other ancillary equipment.

There has been disclosed the best and preferred modes of the invention. The foregoing discussion is meant to provide a general explanation of the purpose and concepts of the instant device. The disclosure and drawings are meant to be explanatory of the invention; however, they are not meant to be restrictive. Slight variations in shape and position of the pads, the openings, ridges or v-grooves, perimeter or rail channels and material are anticipated and would fall within the spirit of this disclosure.

Item Listing

This list is provided as an aid to examination and may be included as part of the application at the discretion of the Examiner. It should be noted that items 116–135 (prototype) parallel items 16–35 (preferred embodiment): items with dashes are only to show pairing.

| | |
|---|---|
| 1. | Generally the Instant Device |
| 2. | |
| 3. | |
| 4. | Generally the IV Support Aperture |
| 5. | |
| 10. | Upper Section |
| 11. | Lower Section |
| 12. | Foot/Heel Pad |
| 13. | Torso Pad |
| 14. | Foot/Heel Pad Indention |
| 15. | Torso Pad Indention |
| 16. | Right Side Skid |
| 17. | Left Side Skid |
| 18. | Right Rear Hand Hold |
| 19. | Left Rear Hand Hold |
| 20. | Right Front Hand Hold |
| 21. | Left Front Hand Hold |
| 22. | Right Side Hand Hold-1 |

-continued

| | |
|---|---|
| 23. | Left Side Hand Hold-1 |
| 24. | Right Side Hand Hold-2 |
| 25. | Left Side Hand Hold-2 |
| 26. | Right Side Hand Hold-3 |
| 27. | Left Side Hand Hold-3 |
| 28. | Right Side Hand Hold-4 |
| 29. | Left Side Hand Hold-4 |
| 30. | Right Side Hand Hold-5 |
| 31. | Left Side Hand Hold-5 |
| 32. | Right Side Mid Strap Aperture-1 |
| 33. | Left Side Mid Strap Aperture-1 |
| 34. | Right Side Mid Strap Aperture-2 |
| 35. | Left Side Mid Strap Aperture-2 |
| 36. | |
| 37. | |
| 40. | Middle V-Channel Stiffener |
| 41. | Left Side V-Channel Stiffener |
| 42. | Right Side V-Channel Stiffener |
| 43. | Left Stiffener Void |
| 44. | Right Stiffener Void |
| 45. | |
| 50. | Right Perimeter Stiffening Channel |
| 51. | Upper Right Perimeter L |
| 52. | Lower Right Perimeter L |
| 53. | |
| 54. | Lower Right Skid/Rail |
| 55. | |
| 56. | Right Skid/Rail Stiffening Channel |
| 60. | Left Perimeter Stiffening Channel |
| 61. | Upper Left Perimeter L |
| 62. | Lower Right Perimeter U |
| 63. | |
| 64. | Lower Right Skid/Rail |
| 65. | |
| 66. | Left Skid/Rail Stiffening Channel |
| 116A. | Prototype Left Side Skid-Rear Section |
| 116B. | Prototype Left Side Skid-Front Section |
| 117A. | Prototype Left Side Skid-Rear Section |
| 117B. | Prototype Left Side Skid-Front Section |
| 118. | Prototype Rear Hand Hold |
| 119. | — |
| 120. | Prototype Right Front Hand Hold |
| 121. | Prototype Left Front Hand Hold |
| 122. | Prototype Right Side Hand Hold-1 |
| 123. | Prototype Left Side Hand Hold-1 |
| 124. | Prototype Right Side Hand Hold-2 |
| 125. | Prototype Left Side Hand Hold-2 |
| 126. | Prototype Right Side Hand Hold-3 |
| 127. | Prototype Left Side Hand Hold-3 |
| 128. | Prototype Right Side Hand Hold-4 |
| 129. | Prototype Left Side Hand Hold-4 |
| 130. | Prototype Right Side Hand Hold-5 |
| 131. | Prototype Left Side Hand Hold-5 |
| 132. | Prototype Right Side Mid Strap Aperture-1 |
| 133. | Prototype Left Side Mid Strap Aperture-1 |
| 134. | Prototype Right Side Mid Strap Aperture-2 |
| 135. | Prototype Left Side Mid Strap Aperture-2 |

What is claimed is:

1. An x-ray compatible spine board comprising:

an upper section;

a lower section having a lower right rail axis, a lower left rail axis, a head end and a foot end;

two lower rail U's formed within said lower section contiguous with said respective lower rail axes;

a plurality of V-stiffening channels formed in said lower section aligned along a longitudinal axis extending from said head end towards said foot end said plurality of V-channels extending from near said head end of said lower section to a point approximately two-thirds along said longitudinal axis toward said foot end of said lower section;

wherein said upper section and said lower section are attached one to each other.

2. The device of claim 1 wherein said upper section has an underside and wherein said V-channel stiffening channels attach to said underside of said upper section.

3. The device of claim 1 wherein said upper section has an upper side and an underside further having a torso pad indention formed in said upper side for receiving a torso pad.

4. The device of claim 3 wherein said upper section further has a foot pad indention for receiving a foot pad formed in said upper side of said upper section.

5. The device of claim 4 wherein a torso pad is placed in said torso indention and a foot pad is placed within said foot indention.

6. The device of claim 5 wherein said torso pad and said foot pad are molded from urethane.

7. The device of claim 5 wherein said torso pad and said foot pad are formed from dense visco-elastic material.

8. The device of claim 1 wherein a plurality of IV apertures are formed in said upper side of said upper section contiguous with said outer perimeter thereof.

9. The device of claim 3 wherein said torso pad indentation has an underside and wherein said V-channel stiffening channels attach to said underside of said torso pad indention.

10. The device of claim 4 wherein said torso pad indentation has an underside and wherein said V-channel stiffening channels attach to said underside of said torso pad indention.

11. The device of claim 2 further having a perimeter and having a perimeter channel formed about said perimeter and further comprising additional stiffening materials molded within said perimeter channel.

12. The device of claim 3 further having a perimeter and having a perimeter channel formed about said perimeter and further comprising additional stiffening materials molded within said perimeter channel.

13. The device of claim 11 wherein said spine board is filled with urethane foam.

14. The device of claim 12 wherein said spine board is filled with urethane foam.

15. The device of claim 1 wherein said lower rail U's have an underside and wherein each said underside becomes respectively a right skid and a left skid for the x-ray compatible spine board.

16. An x-ray compatible padded spine board comprising:

an upper section having an upper outer perimeter and an upper side;

a lower section having a lower outer perimeter, a lower right rail axis, a lower left rail axis, a head end and a foot end;

two lower rail U's formed within said lower section contiguous with said respective lower rail axes, each lower rail channel having an underside;

a plurality of V-stiffening channels formed in said lower section aligned along a longitudinal axis extending from said head end towards said foot end said plurality of V-channels extending from near said head end of said lower section to a point approximately two-thirds along said longitudinal axis toward said foot end of said lower section;

a torso pad indention having an underside formed in said upper side of said upper section for receiving a torso pad;

a foot pad indention formed in said upper side of said upper section for receiving a foot pad;

a torso pad placed in said torso indention;

a foot pad placed within said foot indention;

wherein said upper section and said lower section are attached one to each other such that said upper perimeter and said lower perimeter mesh together; wherein each said underside of each rail channel on said lower section becomes respectively a right and a left skid for the x-ray compatible padded spine board; and, wherein said V-channel stiffening channels attach to said underside of said torso indention.

17. The device of claim 16 wherein said spine board is filled with urethane foam.

18. The device of claim 16 further having a perimeter and having a perimeter channel formed about said perimeter and further comprising additional stiffening materials molded within said perimeter channel.

19. The device of claim 16 wherein said torso pad and said foot pad are molded from urethane.

20. The device of claim 16 wherein said torso pad and said foot pad are formed from dense visco-elastic material.

21. The device of claim 16 wherein a plurality of IV apertures are formed in said upper side of said upper section contiguous with said outer perimeter thereof.

22. A padded spine board comprising:

an upper section having an upper side;

a lower section having an underside;

a torso pad indention formed in said upper side of said upper section for receiving a torso pad;

a foot indention for receiving a foot pad formed in said upper side of said upper section;

a torso pad placed in said torso indention;

a foot pad placed within said foot indention;

a pair of segmented rails attached to said underside of said lower section; and, wherein said upper section and said lower section are attached one to each other forming a cavity; and, wherein said cavity may be filled with urethane foam.

23. The device of claim 22 wherein said torso pad and said foot pad are molded from urethane.

24. The device of claim 22 wherein said torso pad and said foot pad are formed from dense visco-elastic material.

25. The device of claim 22 wherein a plurality of IV apertures are formed in said upper side of said upper section contiguous with said outer perimeter thereof.

26. An x-ray compatible spine board comprising:

an upper section having an upper side;

a lower section having an underside, a head end and a foot end;

a torso pad indention formed in said upper side of said upper section for receiving a torso pad;

a foot indention for receiving a foot pad formed in said upper side of said upper section;

a torso pad placed in said torso indention;

a foot pad placed within said foot indention;

a right skid and a left skid attached to said underside of said lower section;

a plurality of V-stiffening channels formed in said lower section aligned along a longitudinal axis extending from said head end towards said foot end said plurality of V-channels extending from near said head end of said lower section to a point approximately two-thirds along said longitudinal axis toward said foot end of said lower section; wherein said upper section and said lower section are attached one to each other.

* * * * *